United States Patent [19]

Lehmann

[11] Patent Number: 5,606,129

[45] Date of Patent: Feb. 25, 1997

[54] PROCESS FOR SCANNING INSPECTION OF ROTATIONALLY SYMMETRICAL, PARTICULARLY CYLINDRICAL, RECEPTACLES USING A DYNAMIC GAS BEARING, AND INSPECTION DEVICE FOR SAID PROCESS

[76] Inventor: Martin Lehmann, Obere Farnbühlstr. 1, 5610 Wohlen, Switzerland

[21] Appl. No.: 374,904

[22] Filed: Jan. 19, 1995

[30] Foreign Application Priority Data

Jan. 19, 1994 [CH] Switzerland ................. 153/94

[51] Int. Cl.⁶ .................... G01N 29/06; G01N 29/26; G01N 21/90
[52] U.S. Cl. .................... 73/622; 73/640; 73/865.8; 356/237; 356/240; 356/428; 250/223 B; 250/224; 364/507
[58] Field of Search ................ 73/660, 622, 640, 73/642, 620, 865.8; 356/237, 240, 428; 250/223 B, 224; 364/507

[56] References Cited

U.S. PATENT DOCUMENTS

| | | | |
|---|---|---|---|
| 3,415,370 | 12/1968 | Husome | 250/223 B |
| 4,651,568 | 3/1987 | Reich et al. | 73/622 |
| 4,688,427 | 8/1987 | Hyland, Jr. | 73/460 |
| 4,852,415 | 8/1989 | Bogatzki et al. | 73/865.8 |
| 5,255,566 | 10/1993 | Okumura | 73/660 |
| 5,328,018 | 7/1994 | Hoshino et al. | 250/223 B |

FOREIGN PATENT DOCUMENTS

| | | |
|---|---|---|
| 02327294 | 8/1987 | European Pat. Off. . |
| 0232794 | 8/1987 | European Pat. Off. . |
| 2535019 | 2/1977 | Germany . |
| 2930508 | 2/1981 | Germany . |
| 2068550 | 8/1981 | United Kingdom . |

Primary Examiner—Hezron E. Williams
Assistant Examiner—Rose M. Finley
Attorney, Agent, or Firm—Antonelli, Terry, Stout & Kraus, LLP

[57] ABSTRACT

In order to perform all-around inspection of vials in particular, it is proposed that said vials (1) be dynamically mounted in an air-cushion bearing (13) with bearing shells (21a, 21b), that they be rotated with the air of a suction cup (15) that is radially rubber-elastic, and that the vial walls be inspected with the air of a scanning device such as a line camera using working beam (29).

14 Claims, 1 Drawing Sheet

PROCESS FOR SCANNING INSPECTION OF ROTATIONALLY SYMMETRICAL, PARTICULARLY CYLINDRICAL, RECEPTACLES USING A DYNAMIC GAS BEARING, AND INSPECTION DEVICE FOR SAID PROCESS

FIELD OF THE INVENTION

This invention pertains to a process for scanning inspection of rotationally symmetrical, particularly cylindrical, receptacles, as well as an inspection device therefor and a preferred use of said process and said device.

BACKGROUND AND SUMMARY OF THE INVENTION

For ultrasonic testing of workpieces, EP-A-O 232 794, DE-A-25 35 019, GB-A-2 068 550, and DE-A-29 30 508 call for the centering of the workpiece in an acoustic irradiation device centering of the workpiece in an acoustic irradiation device using a gas or fluid cushion. In this connection, e.g., DE-A-25 35 019 or GB-A-2 068 550 also calls for rotating spherical workpieces during acoustic irradiation.

In the manufacture of receptacles, it is frequently necessary, before or after they are filled and, if appropriate, sealed, to check various parameters, e.g., to look for the presence of hairline cracks in the receptacle walls, to check the fill level, the dimensional accuracy of the receptacle, etc.

The inspection processes used in this connection are referred to as scanning processes because a measurement window is always moved along the receptacle wall.

The term "vials" is used to refer to receptacles that are used in particular for pharmaceuticals or medications. They consist essentially of cylindrical glass container bodies that are closed with rubber plugs and whose edges are sealed to the container necks with metal collars. For example, vaccines are drawn from such receptacles by stabbing the injection needle through the rubber plug without breaking the seal on the vial.

This invention pertains in particular to the scanning inspection of such receptacles but can also readily be used for other rotationally symmetrical receptacles in order to check any of the parameters indicated below.

This description is based hereinafter on the preferred vial example, but without prejudice to its applicability to other receptacles.

In the case of the above-mentioned vials, there is a need, particularly after they are filled and sealed, to check the glass wall of the receptacle body for microcracks and/or to check whether the receptacle body is within prescribed dimensional tolerances. The inspection of the above-mentioned dimensional accuracy and the checking for the presence of microcracks in the receptacles call for an all-around inspection of the receptacle such as by scanning inspection. Even if the specified dimensional tolerances are observed, however, as regards their cylindricity such receptacles exhibit relatively large tolerable deviations in roundness from copy to copy; to a very large extent this makes it impossible to determine the geometrically exact location of their axis of rotation.

When performing all-around inspections of such receptacles, however, the obvious approach is not to move the inspection device around a stationary receptacle but rather, specifically because these receptacles are at least approximately rotationally symmetrical, to place the receptacles in front of a fixed inspection device and rotate them to perform the all-around inspection.

It would be possible to attempt to rest the above-mentioned approximately rotationally symmetrical receptacles on roller with axes of rotation essentially parallel to surface lines of the cylindrical receptacles, rotate them, and check the receptacle walls and their fill levels using, in particular, a non-contact inspection device such as a line camera, laser transmission or reflection units, photoelectric barrier units, etc. In this process it would be found that, particularly due to the lack of circularity that is still within tolerance, the mechanically defined placement of the container cylinder wall on rollers leads to inspection results that are at least only conditionally reliable.

An object of this invention is therefore to create a corresponding inspection process and a corresponding inspection device which can be used to obtain reliable inspection results on receptacles of the above-mentioned type despite relatively large shape-dimension tolerances.

For this purpose, the process of the invention is a process for scanning, particularly cylindrical receptacles, comprising arranging a receptacle on an air bearing along its surface line and rotating the receptacle essentially around it axis, and checking the receptacle with the aid of a scanning device that is kept stationary with respect to the rotational motion of the receptacle. An inspection device according to the invention for rotationally symmetrical receptacles, particularly cylindrical receptacles, comprises an air-cushion mounting for the surface line of a receptacle with compressed air discharge for bearing air; a rotation drive for the air-cushion-mounted receptacle; and a scanning unit for the receptacle. The preferred use of the above-mentioned process and device is for inspection of transparent glass receptacles, particularly vials for the presence of wall hairline cracks and/or dimensional accuracy.

Because, according to the process, the receptacles rest on air cushions along their surface lines and are rotated essentially around their axes of rotation, the installed air pressure of the cushion ensures that the receptacle is kept symmetrical owing to an equilibrium of forces at the receptacle wall, i.e., the receptacle is kept symmetrical relative to its outer surface, thus ensuring that a deviation from circularity, which by itself is entirely tolerable, is compensated optimally; this pertains to the "wobbling" of the outer wall during the rotation of the receptacle: rotation takes place without a defined axis position.

Preferably, the air cushion is essentially arranged around the surface line of the rotationally symmetrical receptacle, thus optimally ensuring the above-mentioned symmetry of the radially acting forces on the surface line.

With allowance for the fact that the dynamic air bearing of the type mentioned (which is understood to include, if appropriate, a bearing with another bearing gas as well), the rate of low of the air in the bearing gap leads to an underpressure there and a receptacle will be pushed against the bearing shell, but it is entirely possible to arrange (the receptacle) along a surface line which encompasses an angle of less than 180°.

In order to avoid at least partially disrupting the above-mentioned peripheral arrangement due to the action of a rotational drive, e.g., a mechanical frictional action on the receptacle surface line, in another preferred embodiment of the process a rotation-drive action for the receptacle is provided on the receptacle base, preferably in an approximately axial direction.

In this connection, in another preferred embodiment the optimization of the symmetrical arrangement of the air cushion, which can take effect on its own, is directly exploited owing to the fact that the above-mentioned rotation drive action, which is preferably applied at the receptacle base, occurs elastically at least in the radial direction, thus making allowance for the fact that no axis of rotation actually exists at the receptacle.

Preferred embodiments of the device of the invention, with the advantages just discussed in connection with the process, involve the use of an air-cushion bearing mounting which has a pair of bearing shells that are clamped against one another by springs. The rotation drive for the air-cushion-mounted receptacle has a drive shaft which acts on the receptacle base essentially coaxially, and can thus be brought into frictional contact with the receptacle base. The drive shaft is elastic at least in the radial direction, preferably at the end.

The device further includes an inspection unit, particularly a scanning unit. A relative drive is provided in order to displace the receptacle with respect to the inspection unit essentially parallel to the approximate axis of rotation of the receptacle. In such case the inspection unit is preferably a line camera, laser unit, or photoelectric barrier unit for transmission or reflection measurement.

The process of the invention and the device thereof are particularly suitable for the inspection of vials, and most particularly during their in-line accumulation in production. More basically, however, this process and device are suitable for the inspection of rotationally symmetrical glass receptacles, as well as, if appropriate, for the inspection of rotationally symmetrical receptacles that are made of other, non-transparent materials, e.g., for checking whether form-dimension tolerances are observed or not. Due to the low-friction air-cushion arrangement, receptacles can be rotated at high speed, thus making it possible to conduct the inspection quickly and therefore extremely economically.

The invention is explained below with reference to the figures.

BRIEF DESCRIPTION OF DISCLOSED EMBODIMENT

Figure 1:
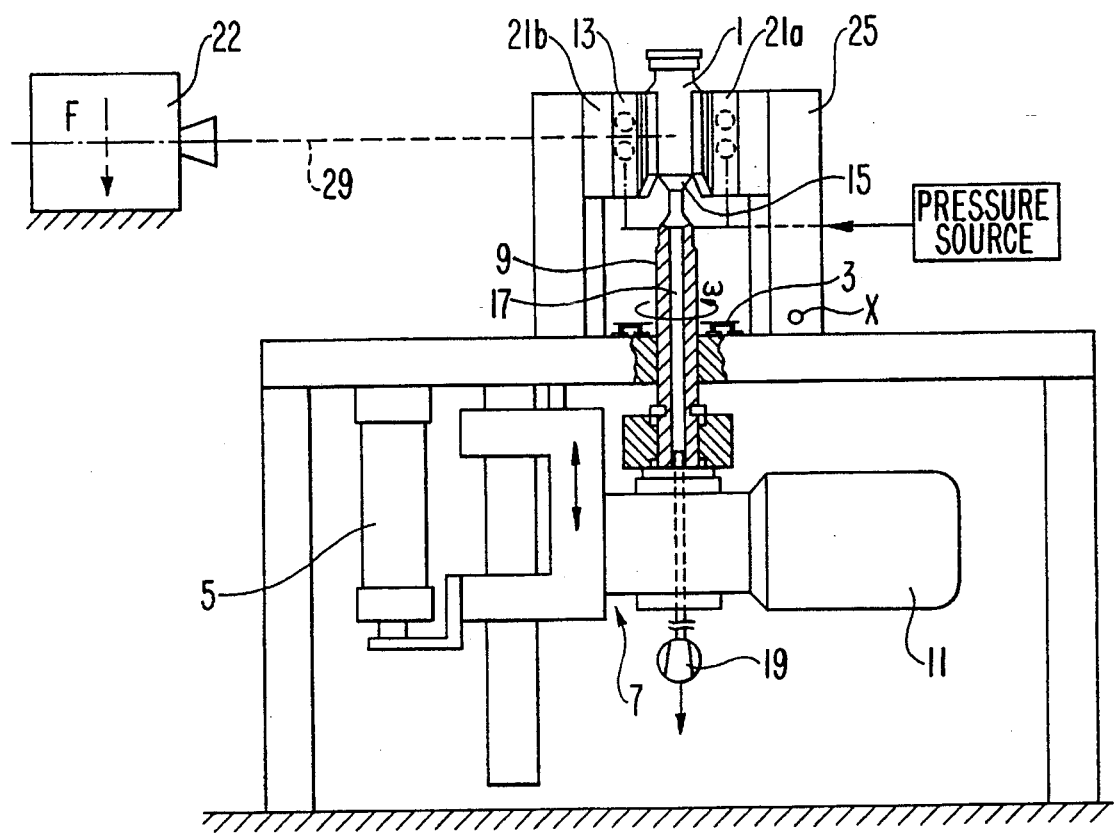
FIG. 1 shows, in simplified form, a partial section of an inspection system with an inspection device according to the invention, which works according to the process of the invention.

As indicated in FIG. 1, vials 1 are supplied by means of, e.g., a schematically depicted conveyor belt 3 in direction x. At the inspection device there is a vertical slide 7 which is driven in a controlled manner by, e.g., a pneumatic drive 5 and which has a drive spindle 9 that projects vertically; said spindle is driven by a drive motor 11. If in each case a vial 1 is aligned to the axis of drive spindle 9, the spindle is lifted with vertical slide 7, thus causing vial 1 to be raised by conveyor belt 3 into the air bearing arrangement 13.

As its end spindle 9 has a suction cup 15 which is rubber-elastic, particularly in the radial direction, and whose inside is connected to a suction line 17 that is attached to suction source 19. By attaching cup 15 to the base of vial 1 by suction, the latter is clamped to air bearing 13 when it is raised by conveyor belt 3.

Once vial 1 has reached the position indicated in FIG. 1, then, in a way to be described below, air bearing 13 is coated with compressed air, and drive spindle 9, and thus vial 1 in air bearing 13, is rotated by means of motor 11. With the aid of an inspection device 22, the wall of the vial is inspected for, e.g., the presence of hairline cracks, in which process either with vertical slide 7 vial 1 is displaced axially in the air bearing during inspection, in such a way that inspection device 22 is able to scan the wall area presented to it, or, as indicated by the dotted line at F, inspection device 22 is displaced parallel to the axis within the framework of the lift that is required for this purpose. Preference is given to the variant where vial 1 is moved axially over drive spindle 9 with vertical slide 7 during receptacle inspection.

Figure 2:
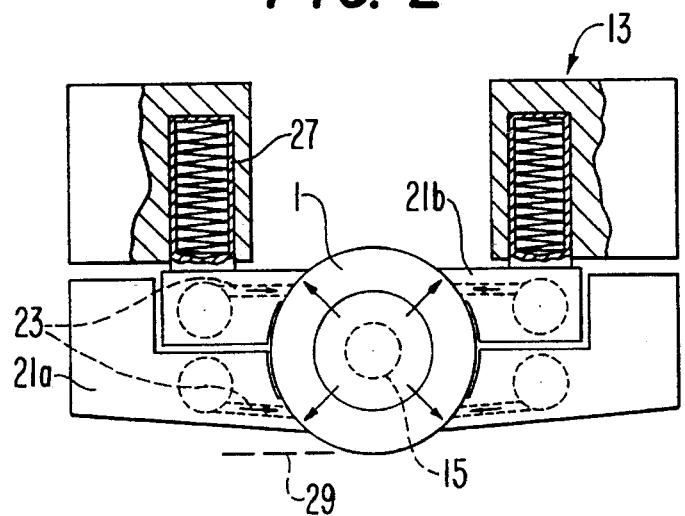
FIG. 2 shows a more detailed top view of an air bearing system used according to the invention, in a preferred embodiment.

FIG. 2 shows a top view of dynamic air bearing arrangement 13 of FIG. 1 in a preferred embodiment. This embodiment comprises two bearing shells 21a and 21b into which compressed-air lines 23 empty respectively, while one of said bearing shells, 21a, is rigidly mounted on frame 25 of the testing station as shown in FIG. 1, and second bearing shell, 21b, is preclamped against the first shell with the aid of springs 27. This makes it possible, when vial 1 is forced upward into air bearing 13, for both bearing shells 21 to be placed as close as possible to the receptacle cylinder surface line.

When compressed air strikes the bearing shells, then, as shown qualitatively in FIG. 2, forces are produced that act on said surface line in an essentially radially outward direction, as a result of the distribution of pressure, and the vial is then held dynamically suspended in the air bearing, while being kept symmetrical by the equilibrium of forces at its surface line. At the same time as (the receptacle) is kept optimally symmetrical, of course, the bearing forces reacting from the bearing on vial 1 are minimized with respect to the rotation drive.

In the figures, 29 indicates the working beam, drawn in by way of example, of a laser scanning device or a line-image camera at unit 22.

I claim:

1. A process for scanning inspection of receptacles, the outer surface thereof defining circles in cross-sectional planes perpendicular to an axis which is perpendicular to a bottom surface of said receptacle, comprising the steps of:

introducing a receptacle into a bearing arrangement having bearing surfaces extending along said outer surface of said receptacle and defining in each cross-sectional plane a circle of larger diameter than the circle defined by said outer surface in such a cross-sectional plane;

injecting a gas from said bearing surfaces of said bearing arrangement towards said outer surface of said receptacle so as to floatingly centralize said receptacle between said bearing surfaces of said bearing arrangement;

rotating said outer surface of said receptacle within said bearing arrangement along said bearing surfaces;

scanning said rotated outer surface by means of a scanning unit provided stationarily with respect to said bearing arrangement.

2. The process of claim 1, further comprising the step of providing said bearing surfaces of said bearing arrangement substantially all around said outer surface of said receptacle.

3. The process of claim 1, further comprising the step of coupling the bottom surface of said receptacle within said bearing arrangement to a rotatably driven axle.

4. The process of claim 3, further comprising the step of coupling said bottom surface of said receptacle to said axle via a coupling member which is elastic.

5. The process of claim 4, further comprising the step of coupling said bottom surface to said elastic member by suctioning.

6. An inspection arrangement for scanningly inspecting receptacles with a bottom surface and an outer surface, said outer surface defining circles in respective cross-sectional planes parallel to said bottom surface, said arrangement comprising:

a bearing arrangement with bearing surfaces defining a bearing chamber rotationally symmetric with respect to a central axis of said bearing chamber so as to define a gap with respect to said receptacle introduced in said cavity;

injection nozzles along said bearing surfaces and connected to a source of pressurized gas;

a drivingly rotatable arrangement as a rotatable abutment member for the bottom surface of said receptacle when introduced;

a scanning unit rigidly coupled to said bearing arrangement.

7. The arrangement of claim 6, wherein said bearing surfaces of said bearing arrangement are formed by at least one pair of jaws.

8. The arrangement of claim 7, wherein the jaws of said pair of jaws are spring-biased towards each other in a direction parallel to a plane comprising said central axis.

9. The arrangement of claim 6, further comprising an elastic coupling member on said shaft for contacting the bottom surface of a receptacle introduced into said cavity.

10. The arrangement of claim 6, wherein the position of said scanning unit is shiftable substantially parallel to said central axis.

11. The arrangement of claim 6, wherein said scanning unit is one of a line camera, a laser unit, a photoelectric scanning unit.

12. The arrangement of claim 6, wherein said scanning unit comprises a light emitter unit and a receiving unit for light one of transmitted and of reflected from an introduced receptacle.

13. The arrangement of claim 6, wherein said cavity has the shape of a vial.

14. A process for scanning inspection of an outer surface of an at least approximately rotationally symmetrical receptacle, said process comprising the steps of positionally supporting an at least approximately rotationally symmetrical outer surface of said receptacle with a dynamic gas bearing while said receptacle is rotatably driven about an axis perpendicular to a bottom surface of said receptacle by a rotatable drive which is elastically coupled, at least in the radial direction, to said receptacle, and scanning an outer surface of said rotating receptacle by means of a scanning unit.

\* \* \* \* \*